(12) United States Patent
Friedlander (10) Patent No.: US 6,347,242 B1
(45) Date of Patent: Feb. 12, 2002

(54) APPARATUS FOR MEASURING OCCULAR CHOROIDAL BLOOD FLOW

(76) Inventor: Lewis D. Friedlander, 975 Wadsworth Dr., Atlanta, GA (US) 30318

( * ) Notice: Subject to any disclaimer, the term of this patent is extended or adjusted under 35 U.S.C. 154(b) by 0 days.

(21) Appl. No.: 09/537,119

(22) Filed: Mar. 29, 2000

Related U.S. Application Data

(60) Provisional application No. 60/126,857, filed on Mar. 30, 1999, and provisional application No. 60/128,385, filed on Apr. 8, 1999.

(51) Int. Cl.[7] ............................................. A61B 5/026
(52) U.S. Cl. ....................... 600/431; 600/475; 600/479; 600/504
(58) Field of Search ................................ 600/473, 475, 600/407, 479, 504, 431; 356/28, 28.5; 351/206, 213, 216, 219, 221

(56) References Cited

U.S. PATENT DOCUMENTS 5,394,199 A * 2/1995 Flower ....................... 600/479
5,543,866 A * 8/1996 Van de Velde .............. 351/221
5,900,928 A * 5/1999 Riva et al. ................... 600/479

* cited by examiner

Primary Examiner—Ruth S. Smith
(74) Attorney, Agent, or Firm—Womble Carlyle Sandridge & Rice, PLLC (57) ABSTRACT

A non-invasive method and apparatus for measuring ocular blood flow. Infrared light is directed to the eye fundus by special contact lens. The amount of light energy reflected in detected and recorded. Following the venous injection of a protein bound green dye, the differential light absorption that occurs as the dye passes through the ocular vasculature gives a curve of blood flow which is used to analyze ocular perfusion. Absorption of light in each eye is recorded by a strip chart recorder. The criteria of arrival time, filling, energy absorption change, runoff and symmetry between the two plots are used to judge the ocular flow in each eye.

10 Claims, 4 Drawing Sheets

APPARATUS FOR MEASURING OCCULAR CHOROIDAL BLOOD FLOW

The present invention claims the benefit of priority to U.S. Provisional Patent Application Ser. No. 60/126,857, filed Mar. 30 1999, entitled: "Method and Apparatus for Binocular Fundus Reflectometry", and U.S. Provisional Patent Application Ser. No. 60/128,385, filed Apr. 8 1999, entitled: "Method and Apparatus for Binocular Fundus Reflectometry".

BACKGROUND OF THE INVENTION

This invention relates generally to an accurate, non-invasive method and apparatus for determining ocular blood flow. This invention can be used to differentiate ischemic from nonischemic oculopathies, a distinction which cannot be made always on purely clinical grounds. This invention can be used to assist is selecting those patients with compromised ocular blood flow that may benefit from angiographic evaluation and spare those patients with nonischemic disease from the risk and discomfort of angiography. Knowledge of the vascular state of the ocular fundus may contribute to an understanding of the pathophysiology of many ocular disorders and may prevent stroke and blindness by early detection of vascular disease. A person with vascular problems will have poor blood flow in the eye, and eventually diminished blood flow in the brain. Additionally, the method of this invention can potentially be a benefit in the non-invasive detection of carotid artery occlusive disease in the absence of ocular manifestations.

In general, an apparatus for fundus reflectometry consists of a light source and a photodetector, with the photodetector used to measure the reflection of light from the fundus of the eye. A dye injected into an antecubital vein flows through the retinal and choroidal vessels and is taken up preferentially in the choroidal layer causing increased absorption and therefore less reflection of light to be detected by the photodetector. The change in reflection correlates with ocular blood flow.

In the prior art, the Patent to Flower (U.S. Pat. No. 4,485,820), discloses a method and apparatus for continuously monitoring hemoglobin saturation in the blood of premature infants. A substantial portion of the eye fundus is illuminated by passing at least two frequencies of light through the pupillary opening. One of the wavelengths is the "isobestic" wavelength which is a wavelength at which little or no difference appears in the optical reflectance of oxy-hemoglobin verses reduced hemoglobin. The invention relies on the infant eye which has a retina that is not fully vascularized and does not have significant pigmentation as in the adult eye. The light scattered from the fundus is collected as it passes out through the pupillary opening and its intensity is measured. The circulation of blood in the choroid is unique in that there is little difference between hemoglobin saturation in the choroidal capillaries and that in the choroidal arteries. Calculations known in the art are used to determine blood hemoglobin based on the intensity of scattered light. An accurate representation of oxygen saturation in arterial blood being carried to the brain can then be obtained. The patent discloses a contact lens with fiber optic links to illuminate the infant eye and collect the scattered light.

The Patent to Gardner, et al. (U.S. Pat. No. 4,346,991), discloses a method and apparatus for measuring retinal blood flow by detecting a doppler shift imparted to laser beams intersecting on a portion of a retinal vessel. Two beams of laser radiation are directed along an optical path into eye and scattered radiation is returned along the path into two photomultipliers. The beams are aligned in the eye so that the plane containing them also contains a direction of blood flow to be measured. The two beams of radiation are scattered by blood corpuscles back along the same optical path and the scattered radiation is received and processed to determine a doppler signal from which blood flow velocity in a single retinal vessel can be determined. The patent measures the blood flow velocity in a single retinal vessel and cannot be used to measure numerous vessels which would enable a closer approximation of flow volume in the eye. The retinal vessels have an autoregulatory capacity which may mask perfusion changes, so measurements of retinal flow alone may give false information regarding ocular perfusion. A more accurate estimate of ocular perfusion may be obtained by measuring choroidal flow. Furthermore, asymmetry of flow is a major component in detection of abnormal perfusion. Therefore, a device is needed that employs binocularity to simultaneously measure blood flow in both eyes.

SUMMARY OF THE INVENTION

It is therefore an object of this invention to provide a method and apparatus for binocular fundus reflectometry for use as a diagnostic tool in detecting ocular ischemia by measuring ocular blood flow. Clinical applications include the differentiation of ischemic oculopathies from inflammatory or other nonischemic disorders.

It is a further object of this invention to detect carotid artery disease in the absence of ocular manifestations.

It is a further object of this invention to provide a technique for use in the post-operative evaluation of patients undergoing revascularization procedures such as carotid endarterectomy or extracranial-intracranial bypass surgery. Patients who demonstrate no change in ocular perfusion following surgery may be suspected of having an occluded vessel at the operative site.

It is another object of this invention to obtain ocular flow measurements intraoperatively and postoperatively in the recovery room or in an intensive care unit.

It is a still further object of this invention to determine the effects of pharmocologic agents on ocular blood flow.

The apparatus for binocular fundus reflectometry is comprised of lightweight, flexible fiberoptic cables terminating in special contact lenses, a sensitive silicon chip photodetector, a specially constructed amplifier connected to a computerized dual channel strip chart recorder and an algorithm that reduces or eliminates the effects of artifactual and extraocular motion noise.

The two bifurcated fiberoptic cables, one for each eye, serve to transmit and receive light simultaneously. Use of a flexible fiberoptic cable reduces changes in lens positions produced by slight ocular movements and allows better beam collimation (focusing) than attempting to mount the light source directly on the eye. Each bifurcated cable is connected to an arc lamp which evenly illuminates the common fiber to produce nearly identical outputs at each eyepiece. The lamp is a ten watt broadband tungsten-halogen filament lamp having a maximum emission wavelength near 900 nanometers. The lamp housing intensity incident upon the fiber bundle may be varied. The maximum observed power output at the eyepiece when filtered is approximately 10 milliwatts. A DC power source and isolation transformer eliminate transient electrical fluctuations.

The two silicon photodetectors are each centrally mounted inside the housing of a differential amplifier to prevent interference from outside light. These monolithic, integrated circuits contain both a photodiode and a transimpedance preamplifier. The radiant responsivity is high with a maximum of 60 mV/W in the near infrared spectrum between 800 nanometers and 900 nanometers. Since the changes in reflection are small, the output signal is increased through a differential amplifier to a level suitable for recording on a peripheral device.

BRIEF DESCRIPTION OF THE DRAWINGS

A full and enabling disclosure of the present invention, including the best mode known to the inventor of carrying out the invention is set forth more particularly in the remainder of the specification, including reference to the accompanying drawings wherein.

DETAILED DESCRIPTION OF THE PREFERRED EMBODIMENT

Reference will now be made in detail to the presently preferred embodiments of the invention, one or more examples of which are illustrated in the drawings. Each aid example is provided by way of explanation of the invention, and not meant as a limitation of the invention. For example, features illustrated or described as part of one embodiment can be used on another embodiment to yield yet another embodiment. It is intended that the present invention includes such modifications and variations.

The following detailed description will first address the physical principles of fundus reflectometry, the analytical determination for the reflectogram underlying the operation of the preferred and disclosed embodiment, which is the best mode presently known by the inventor for carrying out the invention, and will then turn to a discussion of the particular embodiment.

The basic principle of reflectometry is that the reflection of light from the ocular fundus will vary with changes in the optical density. Here the optical density is a function of frequency or wavelength, so that reflection is also wavelength dependent. The optical density of the ocular fundus changes as an absorptive dye fills its vasculature. For optimum results, the spectral bandwidth of the incident light must be matched with a dye that provides maximum absorption for that region of the spectrum.

Figure 1:
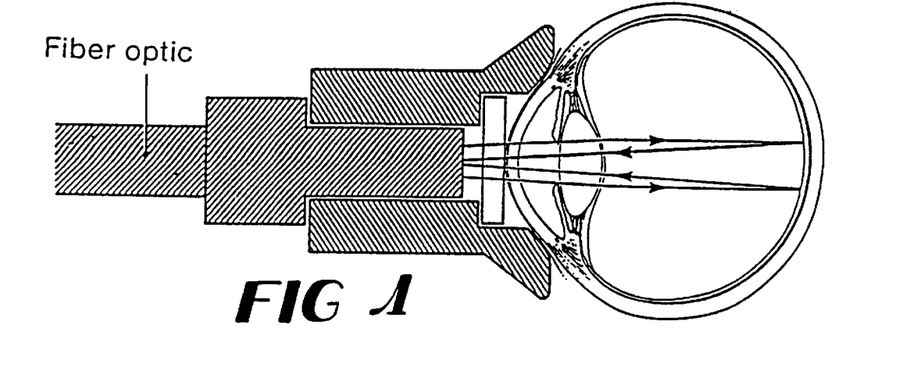
FIG. 1 is a diagram of the contact lens with a single fiber optic cable that simultaneously transmits and receives light.

FIG. 1 shows a contact lens with a single fiber optic cable that simultaneously transmits and receives light. Some attenuation of light occurs in the preretinal media prior to reaching the ocular fundus. This attenuation is due to both true absorption mechanisms and scattering losses and is large (>45%) for wavelengths below 450 nanometers (nm) but decreases significantly throughout the visible and near-infrared spectrum (<900 nm) as shown by curve (a) in FIG. 2. Maximum transmission of ocular media occurs in the region of 600 nm to 900 nm.

In addition to the transmission properties of the ocular media, those of hemoglobin and oxyhemoglobin must also be considered. For wavelengths below 750 nm, the transmission of hemoglobin differs from that of oxyhemoglobin. This difference in transmission below 750 nm probably arises from differences in optical scattering properties of both hemoglobin and oxyhemoglobin. In the near-infrared spectrum between 700 nm and 900 nm, the transmission of each is similar. It is assumed that no resonant spectral structure occurs for either hemoglobin or oxyhemoglobin in the region of 700 nm to 900 nm. As deoxygenation occurs in the ocular fundus, the intensity of reflected light in the near-infrared would, thus, remain nearly constant. Therefore, changes in the reflectogram due to oxygenation properties of hemoglobin are eliminated by measuring reflection in the near-infrared region.- The bandpass filter used has a flat transmission of approximately 94% in the near-infrared spectrum between 700 nm and 900 nm as shown by curve (b) in FIG. 2.

The dye indocyanine green is injected into the bloodstream via an antecubital vein. Upon circulation, the dye passes through the carotid and ophthalmic arteries into the choroidal vasculature of the ocular fundus. The peak spectral absorption is between 800 nm and 810 nm when in blood. The transmission properties of indocyanine green are shown by curve (c) relative responsivity of the photodetector is shown by curve (d) in FIG. 2. The shaded region represents the relative sensitivity of the optical system with maximum detectivity between 800 nm and 820 nm.

Figure 2:
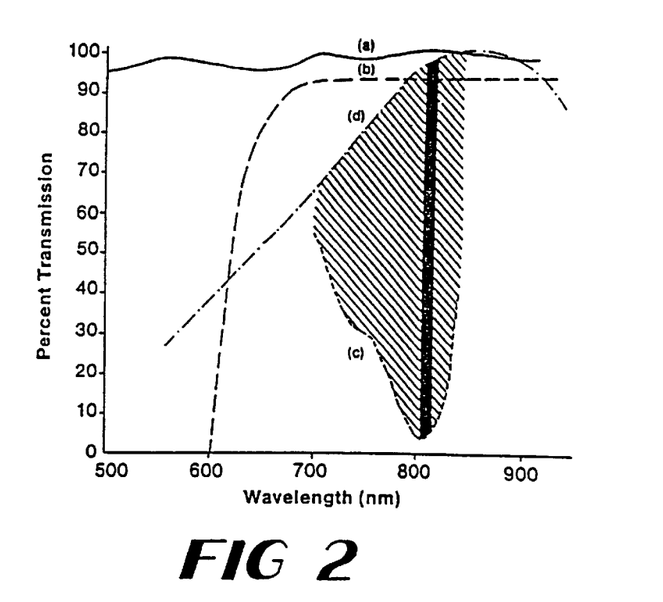
FIG. 2 is a graph of the relative transmission of fiberoptics, a bandpass filter, and cardio-green dye and the relative responsivity of the photodetector.

The actual concentration of indocyanine green at the ocular fundus cannot be easily determined. However, the absorption curve (c) in FIG. 2 is for a serum solution containing 0.005 mg/ml of dye, and since about 4 ml of a 12.5 mg/ml aqueous solution is injected, it is assumed that the concentration reaching the choroid will have sufficient filtering effects even when considerable dilution occurs.

Indocyanine green possesses other beneficial characteristics aside from meeting the above spectral requirements. This dye is nontoxic and has a history of few complications when administered properly. Its hepatic uptake is fairly rapid, with a biological half-life or 2.5 to 3.0 minutes and is completely eliminated shortly after 30 minutes. However, clinical measurements can be repeated in 5 minutes to reproduce the original reflectogram. Indocyanine green is highly bound to blood protein (>98%); thus, once in the choroidal vasculature, excessive dye extravasation does not occur. Choroidal washout occurs rapidly, and recirculation peaks can be observed on the reflectogram. The rapid clearance has the important advantage of allowing several repeated procedures within a short period of time.

While the just described tracer dye is preferred and represents the best mode known to the inventor of carrying out the invention, it nevertheless will be understood that a variety of other tracer compounds might be substituted with comparable results. For example, a fluorescent dye such as fluorescein may be substituted for Indocyanine green and is considered to be within the scope of the invention.

Figure 3:
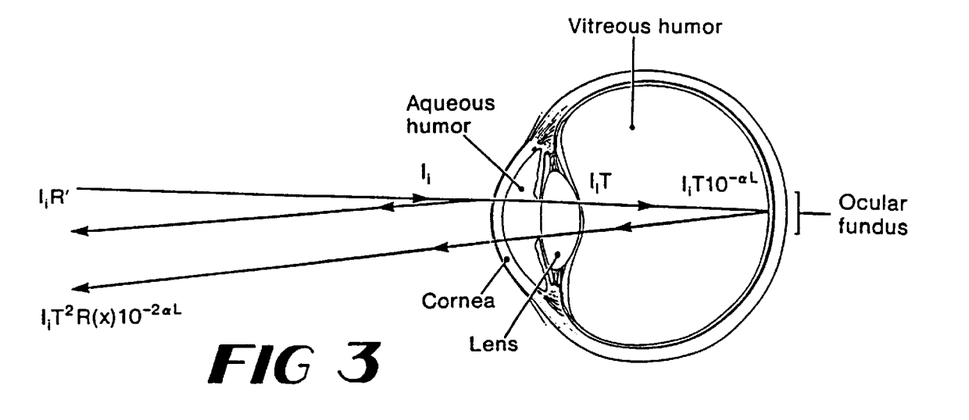
FIG. 3 is a diagram showing that light entering the globe is proportional to the light leaving under constant conditions.

The resulting reflectogram, when plotted on the strip chart recorder, can be viewed as a normalized curve which is a function of the reflection ratio and time. The reflection ratio can be derived with the aid of an ocular diagram, as shown in FIG. 3. The light intensity $I_i$ incident on the cornea undergoes partial reflection and transmission, such that $I_iR'$ is the reflected light and $I_iT$ is the transmitted light. Here $R'$ and $T$ are the power reflection and transmission coefficients, respectively. When passing through the ocular media, both absorption and scattering occur in the preretinal regions and can be combined in a single extinction term. At the retina, the light intensity is given by $I_i 10^{-aL}$, where L is the length of the ocular media and "a" is the extinction coefficient for the combined preretinal media, and is in general wavelength-dependent. Once the light passes through the retina and choroid, it will be reflected by the sclera. Depending upon the optical density of the vasculature, the reflectivity will vary and can be written as $R(x)$, where x denotes the functional dependence of the optical density and hence reflectivity, on dye concentration. The reflected light intensity is then given by $I_i T 10^{-aL} R(x)$. On a second transit through the preretinal media, the intensity becomes $I_i T^2 10^{-aL} R(x)$, where the power transmission coefficient T at the cornea must again be included. In passing the cornea and lens, the interior transmission coefficient may not be the same as the exterior coefficient T and should be written as a different T. However, a different coefficient T would be carried through the calculations and cancelled in the reflection ratio. The final experimental intensity as measured externally to the eye would be given by $$I_f = I_i T 10^{-2aL} R(x) + I_i R' \quad (1)$$

When no dye is present, the intensity can be written $$I_o = I_i T^2 10^{-2aL} R_o + I_i R' \quad (2)$$

where $R_o$ is the maximum reflection coefficient for the ocular fundus in the narrow spectral bandwidth of interest. Small changes in the reflection due to the changing blood volume will be neglected. Observed pulse waves are averaged to yield smooth curves. If the dye concentration were sufficient to absorb all of the incident light (i.e., $R(x)=0$), the total intensity could be expressed by $$I_{oo} = I_i R' \quad (3)$$

This is actually a valid baseline parameter that can be used in calibrating the recorder. Since the actual dye concentrations never reach a value where total absorption occurs, the intensity when dye is present in the fundus can be written $$I(x) = I_i T^2 10^{-2aL} R(x) + I_i R' \quad (4)$$

The intensity due solely to fundus reflection would be $$I_o - I_{oo} = I_i T^2 10^{-2aL} R_o \quad (5)$$

and $$I(x) - I_{oo} = I_i T^2 10^{-2aL} R(x) \quad (6)$$

Dividing the second relation in equation (6) by the first relation in equation (5) yields $$\frac{I(x) - I_{00}}{I_0 - I_{00}} = \frac{R(x)}{R_0} \quad (7)$$

Where $R_o = R(x)$ before injection of the indocyanine dye. The recorder plots this ratio to yield the normalized curves.

Figure 5A:
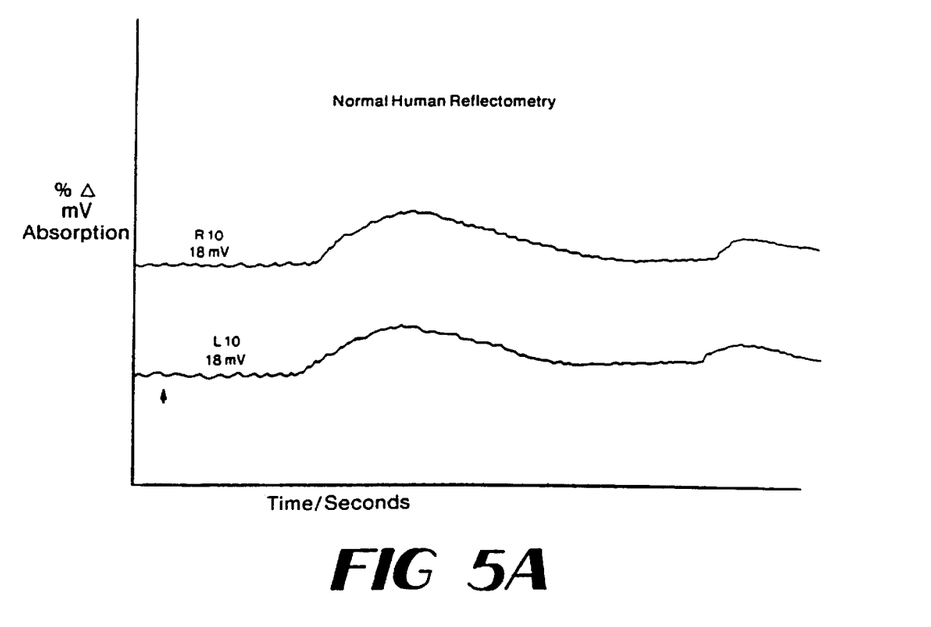
FIG. 5a is a reflectogram showing a symmetric filling and runoff in each eye of a normal human subject.
Figure 5B:
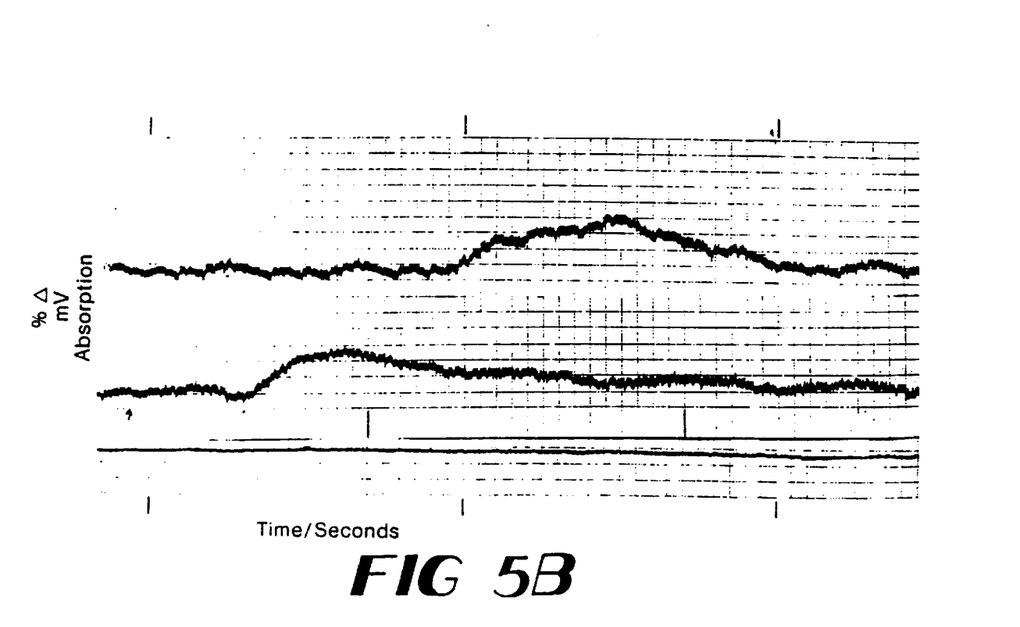
FIG. 5b is a reflectogram showing an abnormal condition in the right eye of a human subject.

Ocular fundus reflectometry was originally used as a technique to measure arm-to-retina circulation time. The described modifications of the system allow an analysis of the total ocular flow curve rather than merely arrival time of the dye. FIG. 5A depicts normal human reflectometry in healthy eyes, whereas FIG. 5B shows an abnormal condition in the right eye of a human subject. The arrival time is considered to be the place where the wave form deviates upward from the baseline. These are calculated for each eye of the patient and compared. The degree of upslope of the curve is also calculated. There may be variability in the upslope due to the speed of bolus injected uniformly in 1-½ seconds. The peak of the change is also recorded as a percentage change from baseline. Finally, the runoff of dye and its slope are calculated. Although there may be theoretical arguments against evaluating these parameters, the uniformity of the technique allows comparison between patients. Differences in the characteristics of curves for each eye indicate disparity of flow. Even with symmetrical flow, bilaterally abnormal patterns can be recognized.

The arrival time of the dye in healthy subjects is usually between 8 and 15 seconds, although the absolute values are far less important than the left-right differences. A difference of 10% or greater would indicate unilaterally impaired circulation. Bilaterally deceased flow would result in abnormally long circulation patterns for both sides.

Figure 4:
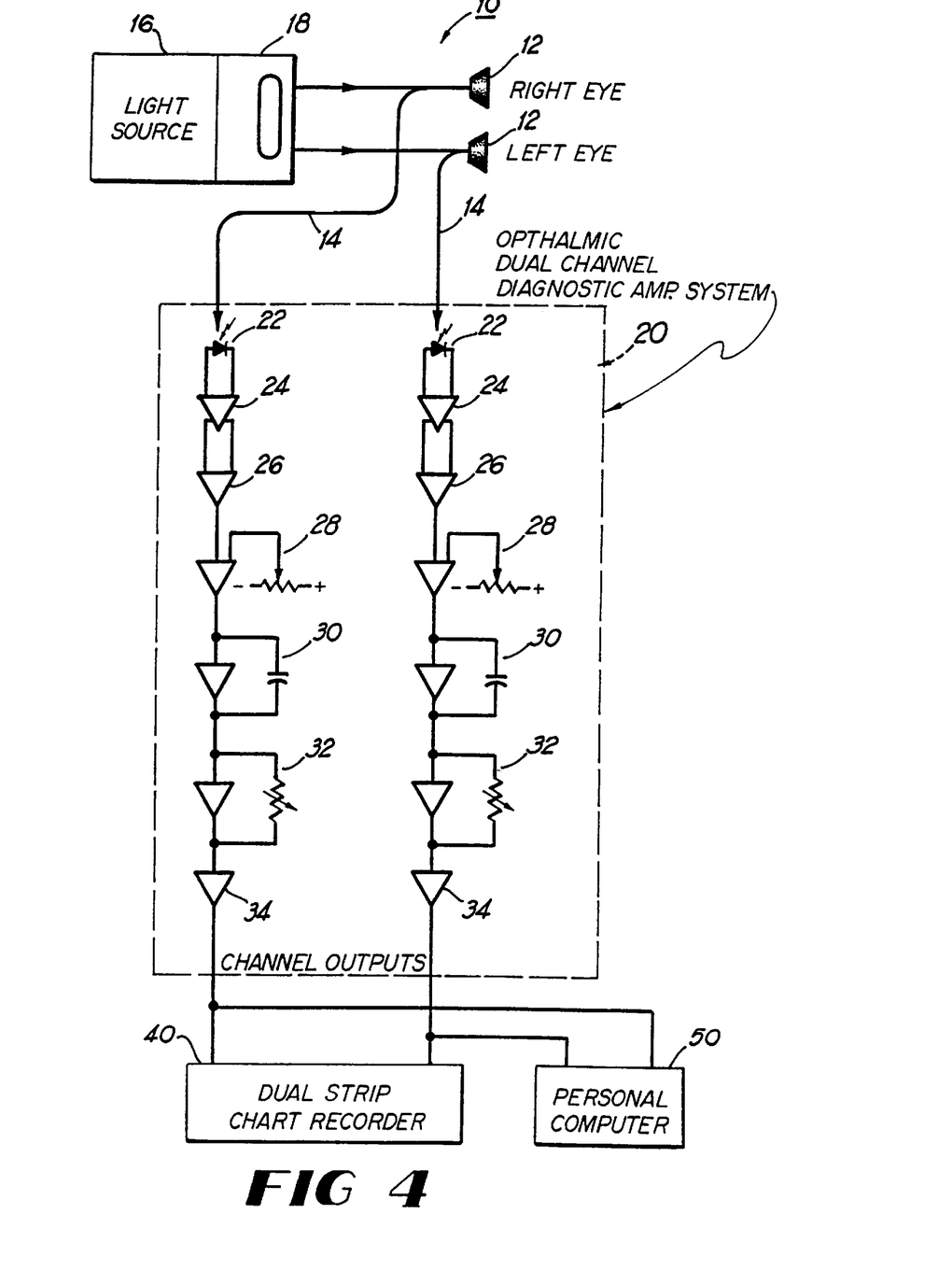
FIG. 4 is a block diagram of the apparatus for binocular fundus reflectometry.

The block diagram of the apparatus for binocular fundus reflectometry 10 is shown in FIG. 4. The system consists of contact lenses 12 which are affixed to the patient's eyes, bifurcated flexible fiberoptic cables 14, light source 16, light filter 18, dual channel diagnostic amplifier system 20, data recorder 40 and personal computer 50. Photodetector 22 is installed in the insulated environment of the diagnostic amplifier housing. The bifurcated fiberoptic cable arrangement is used to take advantage of the unique capability of the fiberoptic cable to transmit light from the light source to the eye and simultaneously carry the reflected light from the eye to the detector through the common branch of the cable. This arrangement results in a loss of roughly 57% of the total transmitted light intensity over earlier nonbifurcated versions. Increasing the transmitted light intensity compensates for the loss through the fiberoptic system.

The eyepieces containing the contact lenses 12 are constructed such that the arrangement of fiberoptics has the ability to project a focus of light energy directly perpendicular to the pupil at all positions of gaze. The recessed contact lens rests on the sclera and conjuctiva but does not contact the cornea and, thus, allows freedom of extraocular motility without interruption or change in recorded signal input or reflected change. The bifurcated fiber optic cables are designed with numerous units of insulated fibers which are spatially oriented to match the projection with reception of energy change at every point of ocular position. The arrangement of fibers are unique in possessing a non-random orientation in the contact lenses 12 and are insulated from each other as separate units to avoid cross current exchange of signal intensity. The avoidance of cross talk makes it possible to clearly delineate the position of greatest signal recording. Thus, a maximum signal without interference from light scattering or change in angle of incident ray is possible in all positions.

Photodetector 22 and detector preamplifier 24 are assembled in the insulated housing of the dual-channel diagnostic amplifier 20 to avoid instability and thermal drift problems. Mounting the photodetector directly on the eyepiece and positioning it adjacent to fiberoptic, termination will result in instability of the signal baseline for up to 5 minutes after placing the eyepiece on the patient's eye. Any handling of the eyepiece with this configuration would cause an even further delay in obtaining a steady baseline due to the thermal drift characteristics of the photodetector's preamplifier relative to its ambient temperature. The change in temperature of the eyepiece produced by touching it would then cause the preamplifier's output signal to elevate along the characteristic drift curve for up to 5 minutes.

Further scattering and absorption losses of reflected light inside the fiberoptic cable necessitate amplifier circuity to compensate for the attenuation, since the change in reflected light due to absorption by the dye is already small. The diagnostic amplifier circuity 20 is designed to provide optimum input sensitivity through the preamplifier 24 and differential noise filter 26. The signal to noise ratio (SNR) in this system is be unusually small, so the noise filter is essential to achieve the largest SNR possible with this optical system. With the eyepiece in place, the signal window median 28 in each channel is set at pre-injection condition. This allows a maximum amplification of the desired signal in both the positive and negative directions about the window median. The signal in each channel is then passed through a low pass active filter 30 to remove ambient and physiological artifacts, then amplified by a variable high gain amplifier 32 and buffered by output buffer amplifier 34. The high gain amplifier 32 must maintain a steady baseline while accurately amplifying the experimental signal to a level suitable for recording on a peripheral device. Since the system is dual channel, an additional requirement is that the measured light intensities and the overall system amplification factor have to be identical for both channels. The channel outputs are then sent to a data recorder 40 where a strip chart records the change in absorption over time and simultaneously to a personal computer 50 where the channel outputs are processed to determine differences.

One requirement of the photodetector 22 and preamplifier 24 is that any change in the intensity of light, I, reflected from the ocular fundus must produce a linearly proportional change in voltage output, V, (i.e., V/1=constant).

The actual clinical procedure can be completed in about 15 minutes. The pupils are first dilated by instillation of a 1% Mydriacyl solution into the conjunctival sac, followed by instillation of a 0.5% proparacaine hydrochloride solution to obtain corneal anesthesia. With the patient in a recumbent position, the fundus reflectometry lenses 12 are aligned, lowered and positioned on each eye. Methylcellulose is applied inside each lens 12 to decrease the possibility of corneal injury and to provide a seal. By suspending the fiberoptics from stereotactic instrumentation, refinement of the lens positioning can be accomplished such that there is almost zero intraocular pressure change. An elevation of intraocular pressure would be undesirable as it would effect the ocular perfusion pressure (the difference in arterial perfusion pressure and intraocular pressure).

With the lenses affixed 12 to the eyes, the incident light intensity from light source 16 is increased, and the strip chart recorder 40 is calibrated. The dye is rapidly injected into an antecubital vein to maximize its concentration in the blood. The injection point is marked on the strip chart readout, and the circulation time measured is that from the injection point to the point at which the reflection from the ocular fundus minimizes. This happens when the optical density of the choroidal vasculature reaches its greatest value for the spectral range of 600–900 nm. As previously discussed, the indocyanine green dye absorbs heavily in this region, and the transmitted light decreases. The resulting reflectogram is show in FIG. 5*a* for healthy, human eyes demonstrating an initial circulation curve and a recirculation curve. The upper plot is for the right eye and the lower plot for the left eye.

The abscissa represents time in seconds and the ordinate plots percentage change in absorption relative to the baseline for each eye. The arrow indicates the point of injection of the dye. R10 and L10 indicate that the arrival time in each eye was 10 seconds after initiation of injection. After peak absorption, the dye washes out. The additional rise represents a second flow through a diluted bolus. FIG. 5*b* shows a reflectogram for a human subject in which an abnormality causes a delay in arrival time of the right eye (top plot) from the left eye (lower plot).

Figure 6A:
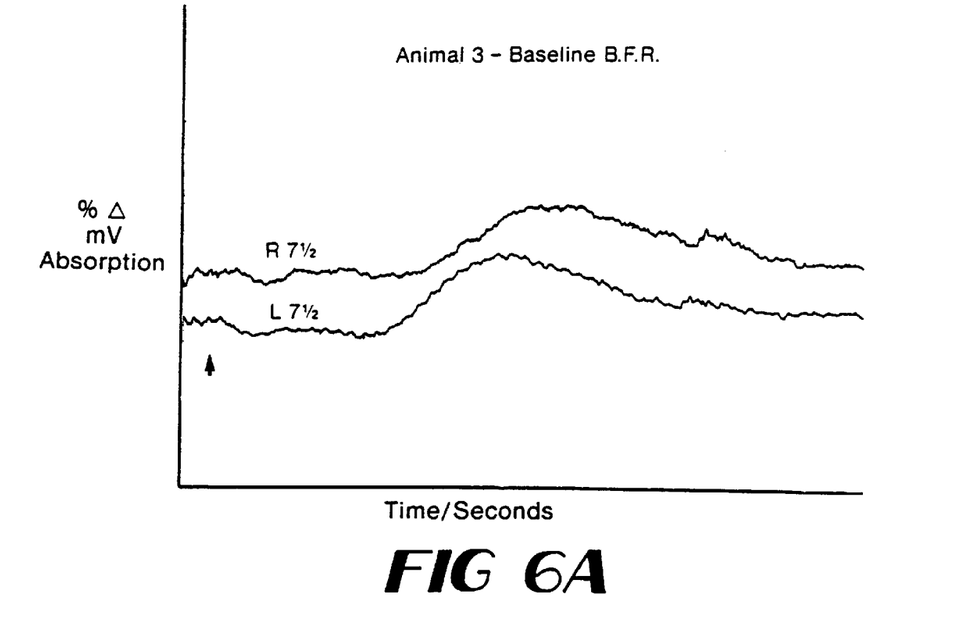
FIG. 6a is a baseline reflectogram showing symmetric filling and runoff in each eye of an animal subject.
Figure 6B:
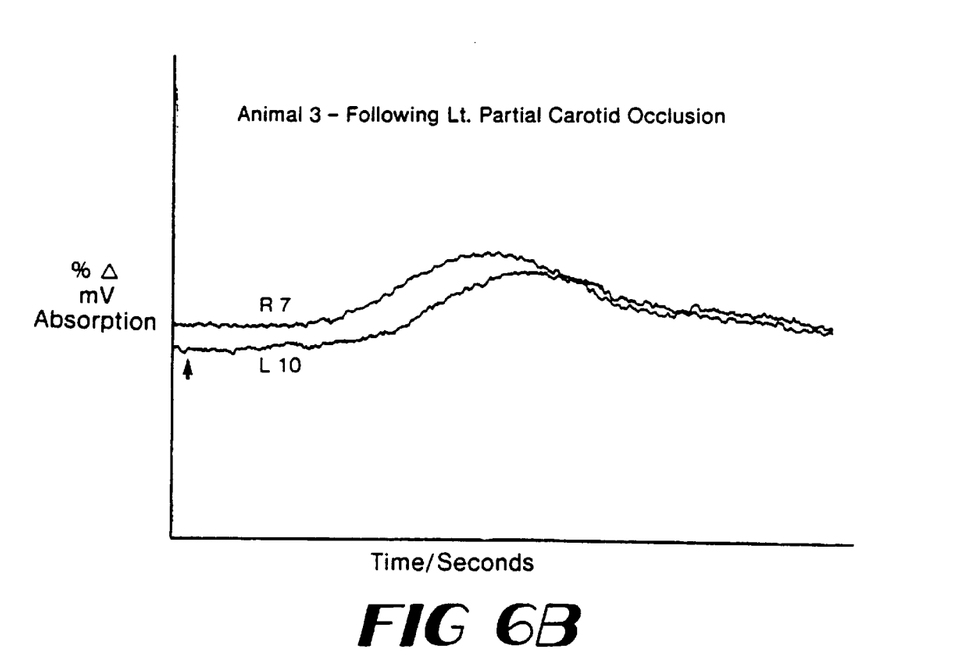
FIG. 6b is a reflectogram showing an abnormal condition in the left eye of the animal subject after a partial carotid occlusion.

FIG. 6 shows examples of binocular fundus reflectograms in an animal test subject before and after experimental occlusion of the common carotid artery. Once the test animal was anesthetized with ketamine (5 mg/kg) and xylazine (0.5 mg/kg), the procedure involved placing an intraveneous line by cut down in the femoral vein. Binocular fundus reflectometry was performed by injecting 2 cc of indocyanine green through the femoral vein line with the animal in the supine position and reflectometry eyepieces held in place with tarsorraphy stitches. The common carotid artery was exposed and temporarily occluded with a vascular clamp, and then the binocular fundus reflectometry was repeated. The pre-occlusion reflectogram is shown in FIG. 6*a* and the post-occlusion reflectogram is shown in FIG. 6*b* . The abnormal condition resulting from the partial carotid occlusion is reflected in the delay in arrival time from 7 to 10 seconds.

The unit contains an auto-injection system to allow uniform injection of the dye in all patients. The injection system contains a pressure transducer and circuit breaker which marks clearly the introduction of dye into the venous system instantaneously and continues injection at a uniform speed. Having a uniform speed of injection allows a comparison of waveforms that is not dependent on human factors of strength reflex or sensation.

The apparatus for binocular fundus reflectometry also contains a separate unit which takes an arterial sample of blood from a peripheral artery and directly samples the concentration of dye at all increments of time during the test period. This allows calculation of volume of dye at all times during testing. By knowing the volume of dilution of dye, the flow rate in the ocular fundus can be calculated as a function of each curve. This unit acts as a shunt intraarterially. By performing this measurement it simultaneously with ocular flow measurements, incremental values of dye concentration can be ascertained instantaneously and recorded. By shunting through the densitometer measurement can be made using standard intravenous disposable tubing. At this time, the simultaneous measurement of blood pressure can be obtained from the arterial shunt line by a pressure transducer. This information is recorded along with heart rate and hematocrit to further analyze the effects of these parameters on blood flow.

The most crucial aspect of interpretation of any signal is the ability to discern noise and artifacts from true physiologic changes. This can be accomplished by the innovative technique of constant signal monitoring and electronic feedback. Considering the task of differentiating a flow change in a curve from one created by a random eye movement, one skilled in the art will realize that electronic balance is the key to clear, true signals. Thus, an algorithm has been devised based on experience with artifactual and extraocular motion noise which ignores these factors and gives a signal derived from the ocular blood flow reflectogram.

Data is taken in two channels from the dual channel diagnostic amplifier 20; one for each eye that are designated as R and L, for right and left eyes respectively. The input to the computer 50 comes directly from the experimental set-up in the form of a set of coordinate pairs for each set of points described (x, y). For each curve, the abscissa, x, is proportional to the time since the injection of the dye and can be converted to such at the end of this algorithm. The ordinate y is a measure of the light reflected off the retina for each eye. Thus, the inputs to the computer are R(x) and L(x).

The first step in the algorithm is to smooth the two functions R(x) and L(x). These two curves are set off from each other both vertically and horizontally. The initial points are superimposed and then the curves are compared. Therefore, after having smoothed the input functions, by looking at the initial point, the vertical offset is determined and subtracted. Next the horizontal offset is determined and subtracted.

The next step in the algorithm is to determine and correct for the inevitable drift that occurs in the measurement of each eye as the experiment progresses. This drift is assumed to be essentially a straight line, and to be the same for each eye. Therefore, the drift in one eye is determined and each point in R(x) and L(x) is corrected for drift.

At this point, an optional step involves displaying these two new functions on the screen monitor of computer 50, since they have been corrected for offsets and drifts. Most likely, the two curves will cross each other several times. This is quite important, and how closely the two curves match each other is a measure of blood flow rate differences. Therefore, the technique is sensitive to when the two curves are about to cross each other. The technique involves defining a new function, F(x), that rises very quickly when R is close to L for a particular abscissa. This function is defined for a particular value of x in the following way:

$$F(x)=1/(|[R(x)/L(x)]|-0.9) \text{ if } R(x)>=L(x)$$

$$F(x)=1/(|[R(x)/R(x)]|-0.9) \text{ if } R(x)>=L(x)$$

Such a function is sensitive to the two functions R and L crossing each other, is never infinite but can be as large as 10 when R=L, and is always positive.

After having computed F(x), a smoothing procedure is introduced for F. The curve is examined on the screen monitor to see where F peaks and how quickly it does so. To see how quickly F peaks at various places, the second derivative of F, namely F" is computed. After having done so, this function is also smoothed and displayed.

By examining those places in F" where F peaks, negative values will be seen. The depth of these troughs is a measure of how quickly F peaks in that place, or in other words how quickly one curve crosses another. Where it does so is an indication of the difference in time that it takes the green dye to be transported in one eye versus the other.

The number of crossings is also important, and this is reflected in the number of peaks in F or the number of troughs in F". Once again, this can be ascertained by visual inspection of either the F of F" graph.

The invention has been described herein in terms of preferred embodiment and methodologies, which represent the best mode known to the inventor of practicing the invention. It will be understood by those of skill in the art, however, that a variety of modifications and substitutions may be within the scope of the present invention. The words used are the words of description rather than of limitation. In addition, it should be understood that aspects of the various embodiments may be interchanged both in whole or in part.

What is claimed is:

1. An apparatus for measuring choroidal blood flow non-invasively and simultaneously in each eye of a subject comprising:

a light source for providing illumination of each eye of the subject over a specific range of frequencies:

a light filter means for bandpass filtering of the illumination from said light source;

a plurality of eyepieces each containing recessed contact lens means for directing the filtered illumination to the choroid and retina of each eye;

a plurality of bifurcated fiber optic cable means each having an input end, an output end and a common end, the input end optically connected to the light source and the common end connected to the eyepiece;

a plurality of photodector means each optically connected to the output end of said bifurcated fiber optic cable means for detecting light signals reflected from the choroid and retina of each eye and which converts said detected light signals into electrical signals;

a plurality of filter means for filtering out said electrical signals which are outside said specific range of frequencies and producing a filtered output;

a plurality of amplifier means for amplifying said filtered output;

recorder means for simultaneously recording each amplified filtered output;

processor means for comparing the amplified filtered outputs and graphically displaying derived outputs which are sensitive to differences between the amplified filter outputs; and an auto-injection system for the introduction of an absorptive dye into the venous system at a uniform speed.

2. The apparatus of claim 1 wherein said light source transmits light having a spectral bandwidth between 600 nm and 900 nm.

3. The apparatus of claim 1 wherein said light filter has a uniform transmissivity between 700 nm and 900 nm.

4. The apparatus of claim 1 wherein said bifurcated fiber optic cable means comprises numerous units of insulated, spatially oriented fibers which are arranged to provide a maximum signal intensity at every ocular position and to avoid cross current exchange of signal intensity between separate units of fibers.

5. The apparatus of claim 1 wherein said auto-injection system further comprises a pressure transducer and circuit breaker which marks the introduction of dye into the venous system and continues injection at a uniform speed.

6. An apparatus for measuring choroidal blood flow non-invasively and simultaneously in each eye of a subject comprising:

a light source for providing illumination of each eye of the subject over a specific range of frequencies:

a light filter for bandpass filtering of the illumination from said light source;

a plurality of eyepieces each containing a recessed contact lens for directing the filtered illumination to the choroid and retina of each eye;

a plurality of bifurcated fiber optic cable means each having an input end, an output end and a common end, the input end optically connected to the light source and the common end connected to the eyepiece;

a plurality of photodectors each optically connected to the output end of said bifurcated fiber optic cables for detecting light signals reflected from the choroid and retina of each eye and which converts said detected light signals into electrical signals;

a plurality of filters for filtering out said electrical signals which are outside said specific range of frequencies and producing a filtered output;

a plurality of amplifiers for amplifying said filtered output; a recorder for simultaneously recording each of said amplified filtered output;

a processor for comparing the amplified filtered outputs and graphically displaying derived outputs which are sensitive to differences between the amplified filter outputs; and an auto-injection system for the introduction of an absorptive dye into the venous system at a uniform speed.

7. The apparatus of claim 6 wherein said light source transmits light having a spectral bandwidth between 600 nm and 900 nm.

8. The apparatus of claim 6 wherein said light filter has a uniform transmissivity between 700 nm and 900 nm.

9. The apparatus of claim 6 wherein each bifurcated fiber optic cable comprises numerous units of insulated, spatially oriented fibers which are arranged to provide a maximum signal intensity at every ocular position and to avoid cross current exchange of signal intensity between separate units of fibers.

10. The apparatus of claim 6 wherein said auto-injection system further comprises a pressure transducer and circuit breaker which marks the introduction of dye into the venous system and continues injection at a uniform speed.

* * * * *